United States Patent
Hsu

(10) Patent No.: US 6,436,076 B1
(45) Date of Patent: Aug. 20, 2002

(54) NEEDLE HOLDER POSITIONING STRUCTURE FOR A SAFETY SYRINGE

(76) Inventor: Fu-Yu Hsu, No.44-1, Potu, Tayuan Hsiang, TaoYuan Hsien (TW)

(*) Notice: Subject to any disclaimer, the term of this patent is extended or adjusted under 35 U.S.C. 154(b) by 62 days.

(21) Appl. No.: 09/738,997

(22) Filed: Dec. 19, 2000

(51) Int. Cl.$^7$ .............................................. A61M 5/00
(52) U.S. Cl. ...................... 604/240; 604/187; 604/239; 604/241; 604/242
(58) Field of Search ................................ 604/187, 239, 604/240, 241, 242

(56) References Cited

U.S. PATENT DOCUMENTS

| | | | | |
|---|---|---|---|---|
| 5,188,599 A | * | 2/1993 | Botich et al. ................ | 604/110 |
| 5,215,533 A | * | 6/1993 | Robb ......................... | 604/195 |
| 5,328,475 A | * | 7/1994 | Chen .......................... | 604/110 |
| 5,405,327 A | * | 4/1995 | Chen .......................... | 604/110 |
| 5,658,257 A | * | 8/1997 | Ryles ......................... | 604/195 |

* cited by examiner

*Primary Examiner*—Charles G. Freay
*Assistant Examiner*—John F Belena
(74) *Attorney, Agent, or Firm*—Rosenberg, Klein & Lee

(57) ABSTRACT

A needle holder positioning structure for a safety syringe includes a syringe with a neck portion having a top end forming a positioning projecting ring, an inner edge of a lower end of the neck portion upwardly and integrally formed with a forked elastic sleeve, with a terminus inwardly forming hook members, a bottom end of a needle holder for receiving a needle being inwardly provided with a flared hole having a distal end forming an enlarged opening, the bottom end of the needle holder being outwardly provided with a guide face, and an outer side formed with depressions corresponding to the hook members.

2 Claims, 8 Drawing Sheets

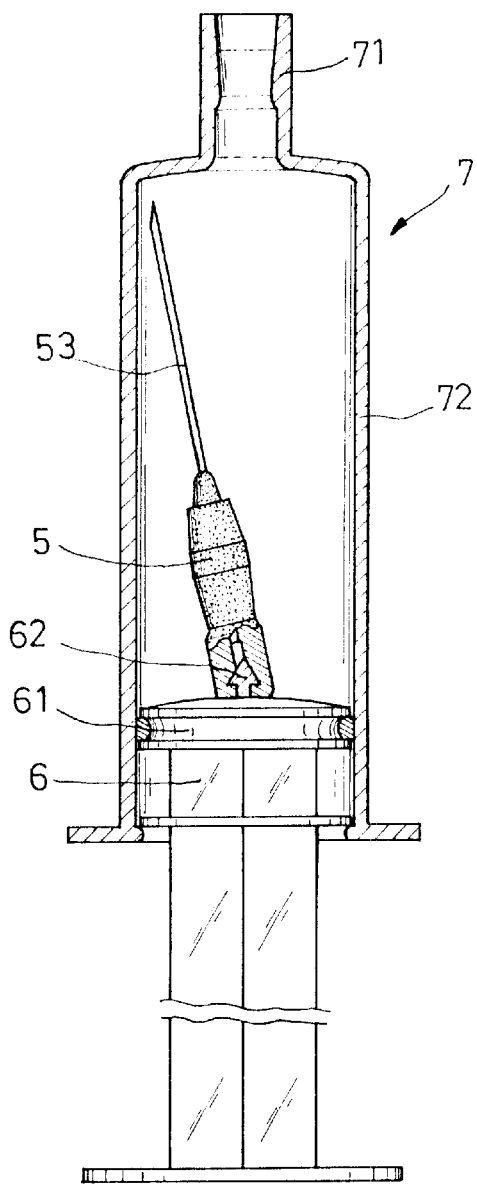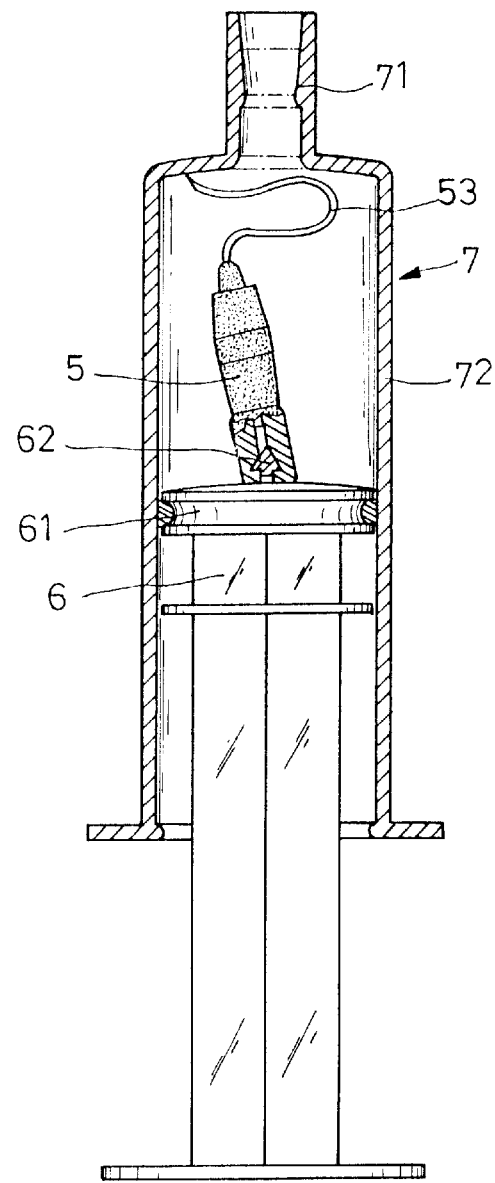
FIG. 9
(PRIOR ART)
FIG. 10
(PRIOR ART)

NEEDLE HOLDER POSITIONING STRUCTURE FOR A SAFETY SYRINGE

BACKGROUND OF THE INVENTION (a) Field of the Invention

The invention relates to a needle holder positioning structure for a safety syringe, more particularly to a low-cost structure that allows precise positioning.

(b) Description of the Prior Art

R.O.C. Patent Publication No. 332433 discloses an improved safety syringe structure having a needle holder positioning structure as shown in FIGS. 6 to 10. A rear end of a needle holder 5 is provided with a flared hole 51 which is enlarged to form an arrow-shaped cavity 52 for receiving an arrow-shaped coupling member 62 provided at the front end of a piston head 61 of a piston 6. After injection, the coupling member 62 and the cavity 52 are coupled integrally. Therefore, when the piston 6 is pulled back, the needle holder 5 together with the needle 53 is disengaged from the neck portion 71 of the syringe 7 to pull the needle 63 into the interior of the syringe body 72 of the syringe 7 so as not to expose on the outside to ensure safety.

Further, since in that patent the needle holder 5 is disposed in the neck portion 71 of the syringe 7, in order that the needle holder 5 can be smoothly pulled back, the needle holder 5 must be formed from elastic rubber material instead of the conventionally used plastic material. However, as rubber is much more expensive than plastic, and the elastic characteristic of rubber may affect the positioning of the needle 53, that patent has the disadvantages of high costs and improper positioning.

There are other related prior art patents, which include U.S. Pat. Nos. 4,932,939, 5,163,907, 5,910,130, 5,879,339, 5,902,277, 5,902,271, 5,902,270, 5,902,269, 5,395,346, 4,737,144, 5,344,403, and 5,569,203.

SUMMARY OF THE INVENTION

The primary object of the present invention is to provide a needle holder positioning structure for a safety syringe, which is inexpensive to manufacture.

Another object of the present invention is to provide a needle holder positioning structure for a safety syringe, which permits precise positioning of the needle.

In order to achieve the above objects, the present invention is characterized in that the inner edge of a lower end of a neck portion of a syringe is upwardly and integrally formed with a forked elastic sleeve and hook members, and a needle holder is corresponding provided with depressions so as to couple the needle holder to the neck portion of the syringe by means of hooking and elastic retention, and the needle holder together with the needle can be pulled back into the interior of the syringe. Furthermore, the needle holder can be made of plastic material. Plastic needle holders are low-cost and permit precise positioning as compared with rubber needle holders.

BRIEF DESCRIPTION OF THE DRAWINGS

The foregoing and other features and advantages of the present invention will be more clearly understood from the following detailed description and the accompanying drawings, in which.

FIG. 9 is a further schematic view showing the process of reverse pulling of the needle holder of Publication No. 332433; and FIG. 10 is still another schematic view showing the process of needle entrapment in syringe casing of the holder of Publication No. 332433.

DETAILED DESCRIPTION OF THE PREFERRED EMBODIMENT

Figure 1:
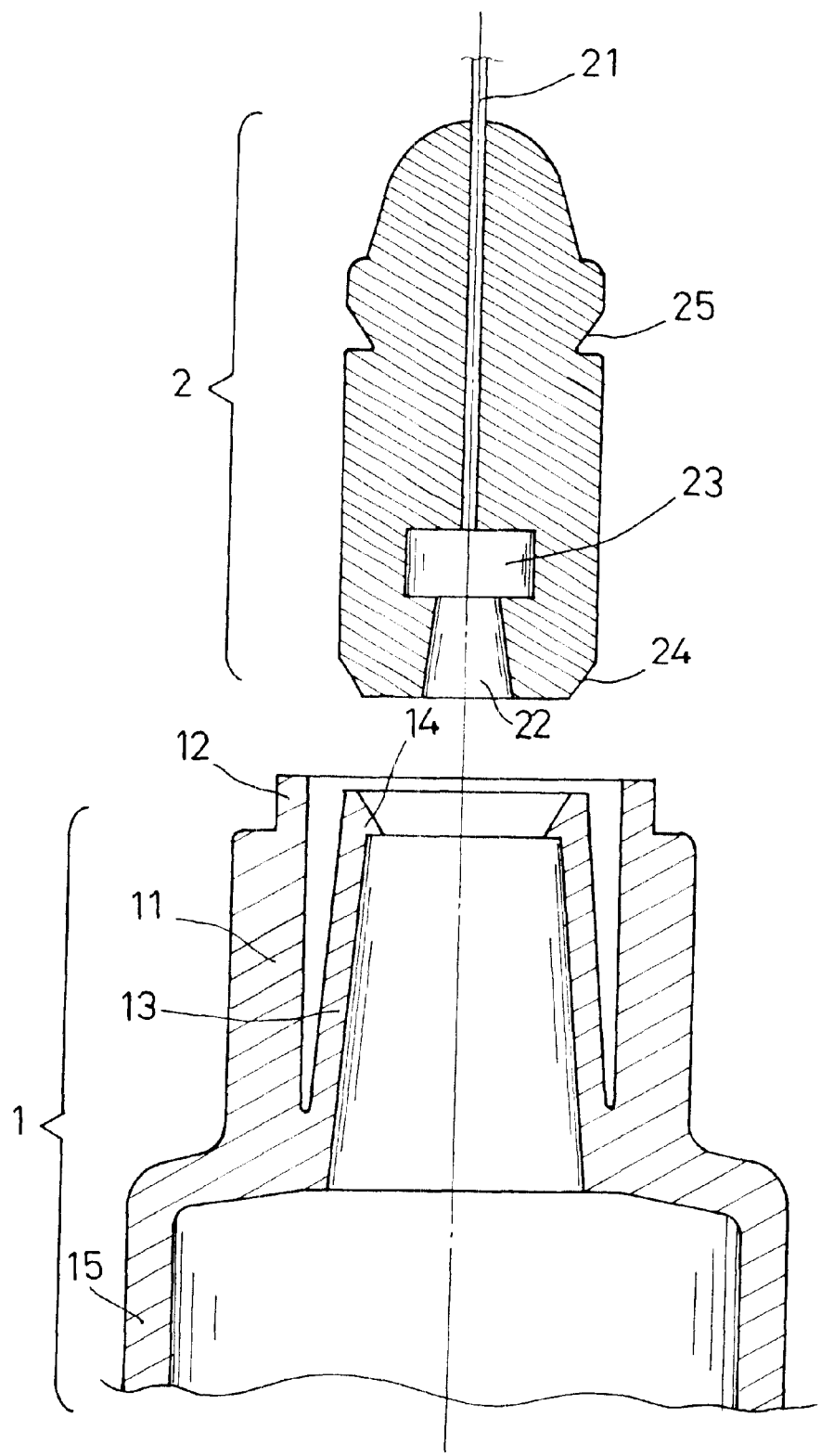
FIG. 1 is a sectional view of the structure of the embodiment of this invention prior to coupling.
Figure 2:
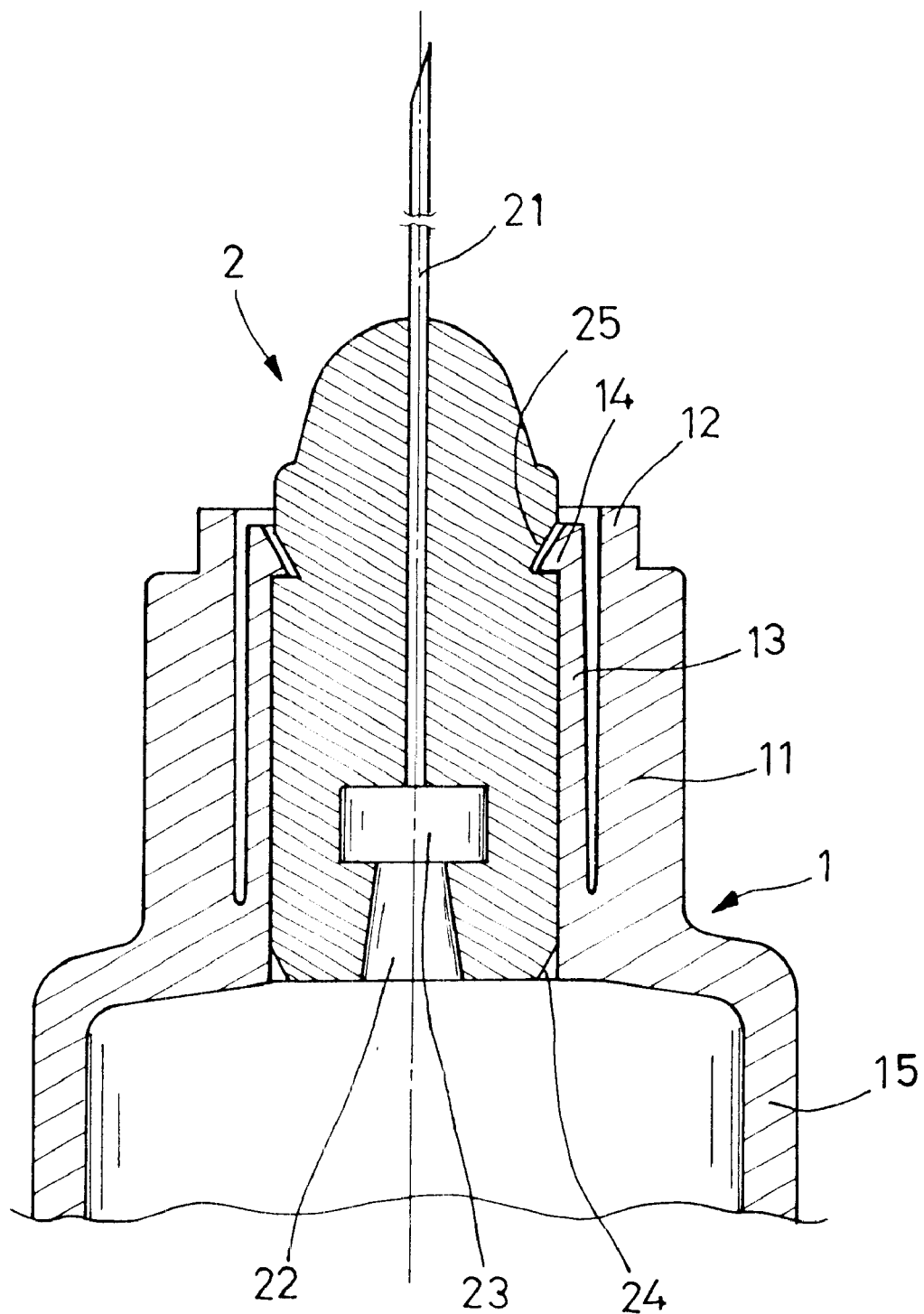
FIG. 2 is a sectional view of the structure of the embodiment of this invention after coupling.

With reference to FIGS. 1 and 2, the invention includes a syringe 1 having a neck portion 11 that forms a positioning projecting ring 12 at a top end. The inner edge of the lower end of the neck portion 11 upwardly and integrally forms a forked elastic sleeve 13, and hook members 14 are formed inwardly at the terminus. The rear end of a needle holder 2 for receiving a needle 21 is inwardly provided with a flared hole 22 with a distal end forming an enlarged opening 23. The bottom end of the needle holder 2 is outwardly formed with a guide face 24, with depressions 25 formed in the outer side to correspond to the hook members 14.

Figure 3:
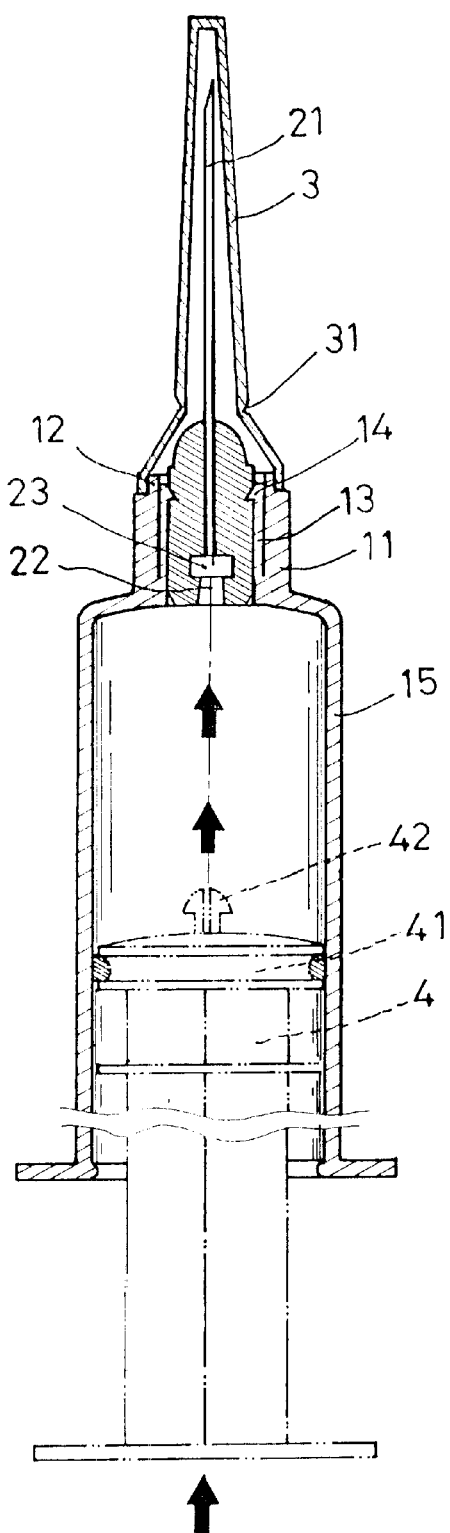
FIG. 3 is a schematic view showing the embodiment of this invention assembled to a safety injection syringe.
Figure 4:
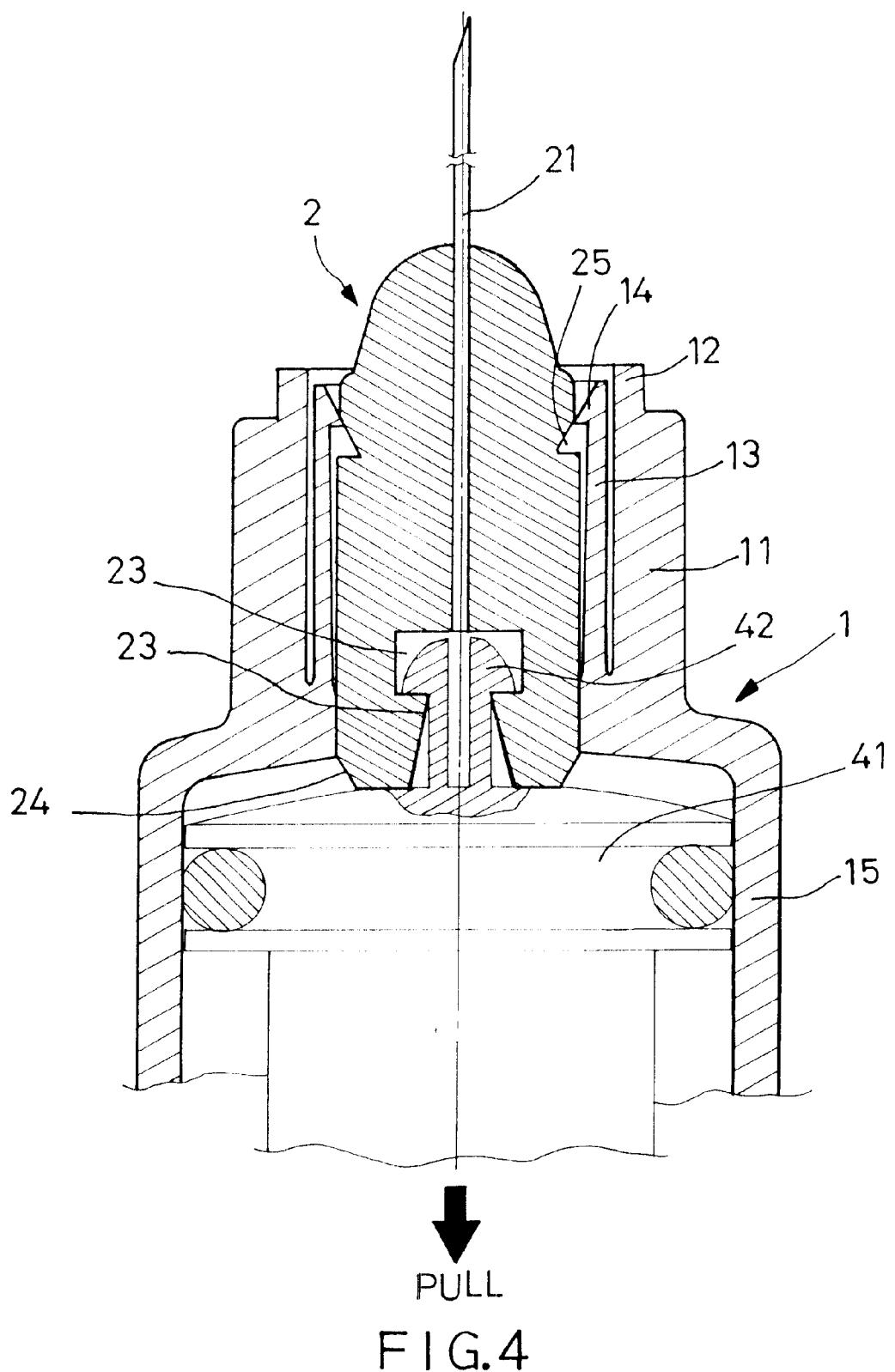
FIG. 4 is a schematic view illustrating pulling back of the embodiment of this invention.
Figure 5:
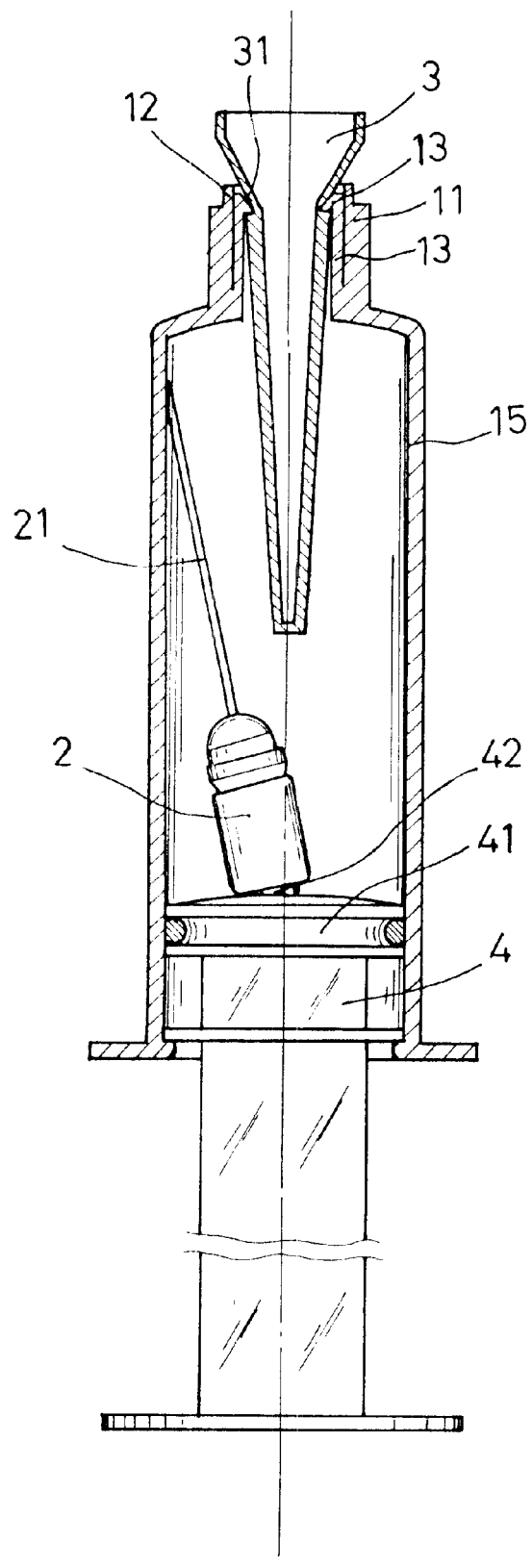
FIG. 5 is a schematic view illustrating reverse fitting of a needle sleeve of the embodiment of this invention.
Figure 6:
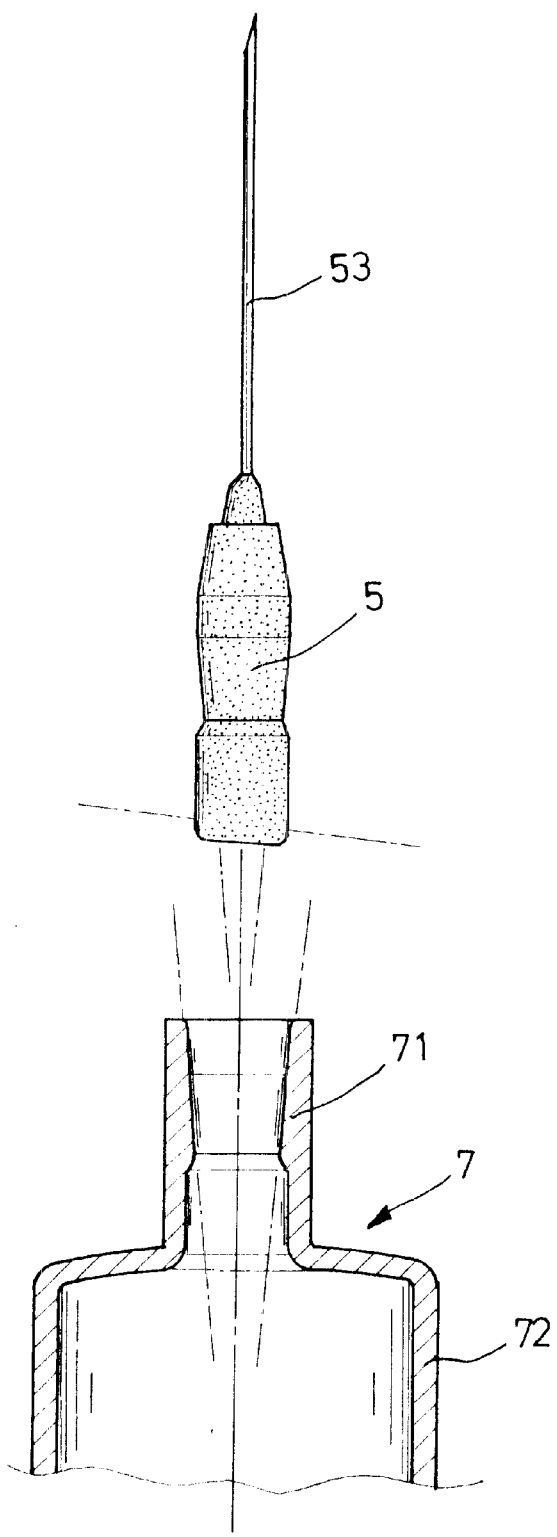
FIG. 6 is a schematic view showing a needle holder positioning structure of Publication No. 332433.
Figure 7:
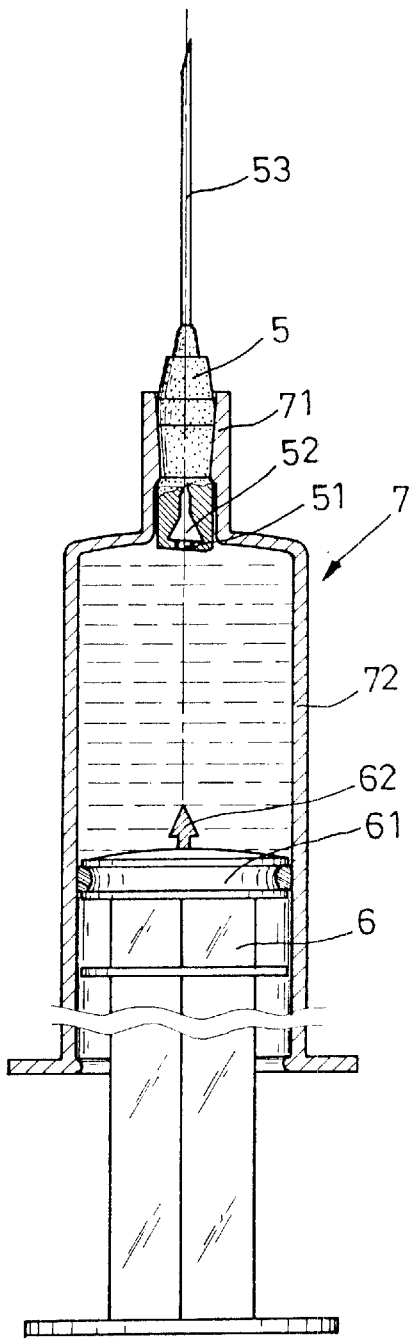
FIG. 7 is a schematic view showing the process of reverse pulling of the needle holder of Publication No. 332433.
Figure 8:
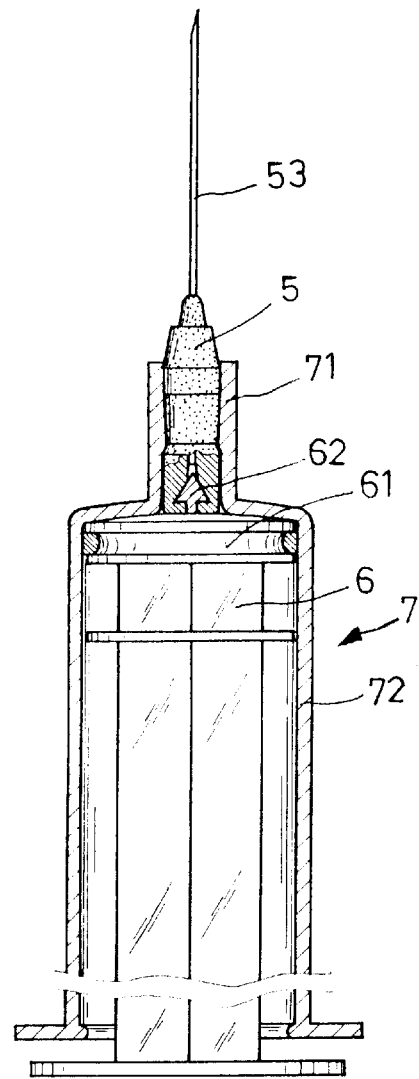
FIG. 8 is another schematic view showing the process of reverse pulling of the needle holder of Publication No. 332433.

With reference to FIG. 3, the positioning projecting ring 12 serves to position a needle sleeve 3. The front end of a piston head 41 of a piston 4 is provided with a coupling member 42 corresponding to the flared hole 22 and the enlarged opening 23 of the needle holder 2 so as to permit retraction of the needle holder 2 with the needle 21. However, as such a structure is not the subject matter of this invention, it will not be described in detail herein. Referring to FIGS. 3 and 5, the outer edge of the needle sleeve 3 is provided with recesses 31 corresponding to the hook members 14. When the needle 21 is pulled back to the interior of a syringe body 15, the needle sleeve 3 is fitted in a reverse direction to cause the recesses 31 and the hook members 14 to come to a retained state, thereby preventing extension of the needle and leakage of possible residual blood in the syringe 1 to ensure safety.

Based on the above construction, the flared hole 22 of the needle holder 2 is configured to be able to retract inwardly and elastically, the guide face 24 guides into the neck portion 11 of the syringe 1, the depressions 25 retain the hook members 14 of the syringe 1, and the elastic sleeve 13 positions the needle holder 2 firmly with its inward retaining force (see FIG. 2). In addition, after injection, when the piston 4 is pulled back (the relationship between the piston 4 and the needle holder 2 being described hereinabove), the back pulling force may offset the inward retaining force of the elastic sleeve 13 to cause the needle 21 to be pulled back into the interior of the syringe body 15. Therefore, this invention employs hooking and elastic retaining force to couple the needle holder 2 to the neck portion 11 of the syringe 1, and is directly formed by plastic injection molding, without the need to use rubber material as in the prior art. This not only reduces costs, the plastic needle holder allows more precise positioning of the needle 21.

Although the present invention has been illustrated and described with reference to the preferred embodiment thereof, it should be understood that it is in no way limited to the details of such embodiment but is capable of numerous modifications within the scope of the appended claims.

What is claimed is:

1. A needle holder positioning structure for a safety syringe, comprising a syringe with a neck portion having a top end forming a positioning projecting ring, an inner edge of a lower end of said neck portion upwardly and integrally formed with a forked elastic needle sleeve, with a terminus inwardly forming hook members, a bottom end of a needle holder for receiving a needle being inwardly provided with a flared hole having a distal end forming an enlarged opening, the bottom end of said needle holder being outwardly provided with a guide face, and an outer side formed with depressions corresponding to said hook members.

2. The needle holder positioning structure for a safety syringe of claim 1, wherein said needle sleeve fitted on said positioning projecting ring has an outer edge provided with recesses corresponding to said hook members.

\* \* \* \* \*